(12) United States Patent
Rajagopalan et al.

(10) Patent No.: US 6,423,547 B1
(45) Date of Patent: Jul. 23, 2002

(54) NON-COVALENT BIOCONJUGATES USEFUL FOR DIAGNOSIS AND THERAPY

(75) Inventors: Raghavan Rajagopalan, Maryland Heights; Joseph E. Bugaj, St. Charles; Richard Bradley Dorshow; Samuel I. Achilefu, both of St. Louis, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/646,765

(22) PCT Filed: Mar. 31, 1999

(86) PCT No.: PCT/US99/07061
§ 371 (c)(1),
(2), (4) Date: Sep. 21, 2000

(87) PCT Pub. No.: WO99/51284
PCT Pub. Date: Oct. 14, 1999

Related U.S. Application Data
(60) Provisional application No. 60/080,658, filed on Apr. 3, 1998.

(51) Int. Cl.$^7$ ................. G01N 33/531; A61K 49/00; A61B 5/055
(52) U.S. Cl. ................. 435/961; 424/9.1; 424/9.34
(58) Field of Search ................. 424/9.1, 9.34; 435/961

(56) References Cited
U.S. PATENT DOCUMENTS
4,806,488 A * 2/1989 Berger, Jr. et al. .......... 436/536

* cited by examiner

Primary Examiner—Hankyel T. Park
(74) Attorney, Agent, or Firm—Lawrence L. Limpus

(57) ABSTRACT

A composition comprising non-covalent carrier-hapten bioconjugates having the formula:

HM-CM wherein HM is a hapten molecule whose molecular weight is generally, but not always, less than 1000 Daltons and is capable of performing specific functions; CM is a carrier molecule, whose molecular weight is generally, but not always, more than 1000 Daltons and is capable of transporting the hapten to a specific site; and the dashed line is a non-covalent bond between the carrier molecule and the hapten molecule.

Preferably, the bioconjugates are formed from fluorescent dye haptens such as cyanine, indocyanine, squaraine, porphyrrins, Rose Bengal, and methylene blue dye and carrier molecules such as methylated serum albumin, polyarginine, polyaspartic acid, polyglutamic acid, cyclodextrin, and inulin.

The bioconjugates are useful in diagnostic and therapeutic medical procedures because they are stable in vitro before being used and stable in vivo during and after use.

30 Claims, 9 Drawing Sheets

NON-COVALENT BIOCONJUGATES USEFUL FOR DIAGNOSIS AND THERAPY

This application claims priority from provisional application Ser. No. 60/080,658, filed Apr. 13, 1998.

BACKGROUND OF THE INVENTION

1. Field of the Invention

This invention pertains to non-covalent-carrier-hapten bioconjugates and their use to selectively deliver diagnostic and therapeutic agents to target tissues and organs. Particularly, this invention pertains to the selective delivery of fluorescent non-covalent carrier-hapten bioconjugates to a specific site for the purpose of determining the structure and function of tissues or organs using optical tomographic imaging procedures, fluorescence monitoring procedures, absorbance monitoring procedures, or endoscopic examination procedures.

2. Description of the Prior Art

Non-covalent intermolecular forces (e.g. electrostatic, hydrogen bonding and Van der Waals interactions) play a vital role in many biological process such as enzyme catalysis, drug-receptor interaction, antigen-antibody interaction, biotin-avidin interaction, DNA double helix formation, phagocytosis, pigmentation in plant and animals, and cellular transport. Variety of colors observed in flowers and plants, for instance, are attributed to non-covalent association between the natural pigments and carbohydrates or proteins found in plant cells.

Non-covalent forces can alter the physicochemical and/or biological properties of haptens or carriers. For example, association of dye or a pigment molecule with proteins or carbohydrates can change the chemical or photo stability, change the intensity and/or the wavelength of absorption/emission maxima, or both. Although the interaction energy per unit interaction is quite small (c.a. less than 40 kJ/interaction), the cumulative effect of multiple points of interaction along the two surfaces can be substantial and can lead to strong binding between the hapten and the carrier. This approach has been successfully used to prepare anti-DNA antibodies. DNA is a highly charged anionic macromolecule that is normally non-immunogenic; but, when it is complexed with a highly charged cationic methylated bovine serum albumin (MBSA), DNA becomes immunogenic. Thus, the non-covalent DNA-MBSA bioconjugate was stable enough to elicit immune response toward DNA.

Non-specific interactions also play an important role in biological processes. For example, human serum albumin binds various molecules in a non selective fashion and facilitates the transport of these molecules across from the vasculature to the cells.

Thus, it is clear from the examples above that the non-covalently attached bioconjugates function biologically as a single unit. In addition to the above mentioned properties, the carrier molecule may also protect some haptens from chemical, photochemical, or radiolytic degradation. The present invention is intended to exploit the concept of non-covalent interactions in the design of novel bioconjugates for diagnosis and therapy.

Further, the use of fluorescent dyes and covalent dye bioconjugates for the detection of various species in the body fluids is well known in the field of in-vitro immunodiagnostics. Dye-immunoconjugates have been widely used in immunohistology, and immunochemical detection of various antigens, hormones, drugs and the like in body fluids via radioimmunoassay (RIA) or enzyme-linked immunosorbent assay (ELISA) procedures. Fluorescent dyes have also been used as chemosensors and in fluorescence microscopy. (J. P. Desvergne and A. W. Czarnik, *Chemosensors of Ion and Molecule Recognition*, Kluver Academic, Boston, 1997; B. H. Satir, Ed., *Noninvasive Techniques in Cell Biology*, Wiley-Liss, New York, 1990). Indocyanine green, a highly fluorescent polyene dye, has been used for monitoring cardiac output, assessing hepatic function, and tomographic imaging of tumors (K. Licha et al., Synthesis and Characterization of Cyanine Dyes as Contrast Agents for Near-Infrared Imaging, *SPIE*, 1996, Vol. 2927, 192–197; X. Li et al., Tumor Localization Using Fluorescence of Indocyanine Green in Rat Models, *SPIE*, 1995, Vol. 2389, 789–798; B. Riefkce et al., In Vivo Characterization of Cyanine Dyes as Contrast Agents for Near-Infrared Imaging, *SPIE*, 1996, Vol.2927, 199–208).

In conventional bioconjugate chemistry, conjugates are prepared by covalent attachment of various effector molecules such as drugs, hormones, radiopharmaceutical agents, magnetic resonance imaging agents, chemotherapeutic agents, and the like to the bioactive carriers. Such a process often involves cumbersome chemical manipulation of the two components, in addition to the complicated synthesis of appropriate activated haptens necessary for covalent attachment. Moreover, the bioactivity of the resulting complex is, in many cases, either greatly diminished or obviated altogether.

Polyene dyes, in general, and indocyanine green, in particular, have several disadvantages that limit their use as near-infrared (NIR) contrast agents. Indocyanine green has a very short plasma half-life and is rapidly taken up by the liver (D. K Meijer et al., Pharmacokinetics of Biliary Excretion in Man. VI. Indocyanine Green, *Eur. J Clin. Pharmacol.*, 1988, Vol. 35, 295–303); has low fluorescence efficiency, and undergoes degradation in aqueous media with loss of fluorescence. Therefore, there is a need for novel bioconjugates that are simple to prepare and stable enough to be useful as a diagnostic or a therapeutic agent.

SUMMARY OF THE INVENTION

It is, therefore, an object of the present invention to provide non-covalent carrier-hapten bioconjugates that are simple to prepare and are useful in diagnostic and therapeutic medical procedures.

It is another object of the present invention to provide bioconjugates that are stable during storage before being used in diagnostic and therapeutic medical procedures.

It is a further object of the present invention to provide a method for performing a diagnostic or therapeutic procedure on a patient.

It is a another object of the present invention to provide a method for altering the blood persistence of a hapten.

It is a another object of the present invention to provide a method for increasing the in vitro and in vivo fluorescent life of a fluorescent dye.

These and other objects are achieved using new and structurally diverse non-covalent carrier-hapten bioconjugates having the formula:

HM-CM wherein HM is a hapten molecule whose molecular weight is generally, but not always, less than 1000 Daltons and is capable of performing specific functions; CM is a carrier molecule, whose molecular weight is generally, but not always, more than 1000 Daltons and is capable of transporting the hapten to a specific site; and the dashed line is a non-covalent bond between the carrier molecule and the hapten molecule.

Preferably, the bioconjugates are formed from fluorescent dye haptens and carrier molecules selected from the group consisting of serum albumin, methylated serum albumin, polypeptides with molecular weight ranges from 2000 to 20000 Daltons, and polysaccharides with molecular weight ranges from 2000 to 20000 Daltons, polynucleotides with molecular weight ranges from 2000 to 100000 Daltons, cyclodextrins, calixarenes, and surfactants.

Most preferably, the bioconjugates are formed from fluorescent dye haptens selected from the group consisting of cyanine, indocyanine, squaraine, porphyrrins, Rose Bengal, and methylene blue dye and carrier molecules selected from the group consisting of methylated serum albumin, polyarginine, polyaspartic acid, polyglutamic acid, cyclodextrin, inulin, polyadenylic acid, and polyguanylic acid.

The bioconjugates are useful as diagnostic and therapeutic agents in medical procedures because they are stable in vitro before being used and stable in vivo during and after use. It is theorized that the bond between the hapten and the carrier stabilizes the bioconjugates and delays its degradation in vitro by environmental factors. Also, the bond causes the bioconjugates to be metabolized slowly in vivo and therefore retained in the body for a longer period than expected for the non-bound hapten.

Other objects, advantages, and novel features of the present invention will become apparent in the following detailed description of the invention.

DETAILED DESCRIPTION OF THE INVENTION

The present invention provides new and structurally diverse non-covalent carrier-hapten bioconjugates having the formula:

HM-CM wherein HM is a hapten molecule whose molecular weight is generally, but not always, less than 1000 Daltons and is capable of performing specific functions; CM is a carrier molecule, whose molecular weight is generally, but not always, more than 1000 Daltons and is capable of transporting the hapten to a specific site; and the dashed line is a non-covalent bond between the carrier molecule and the hapten molecule.

The hapten is either a small molecule or a macromolecule and is selected from the group consisting peptides, carbohydrates, and fluorescent dyes. The hapten can be molecules such as hormones, antibodies, anti-neoplastic agents, enzymes, coenzymes, peptidomimetics, glycomimetics, cell adhesion molecules, radionuclide metal complexes, magnetic resonance imaging agents, X-ray opacification agents, and echogenic agents.

Preferably, the hapten is a dye whose absorption and emission maxima fall in 200–1200 nanometers (nm) range or a photosensitizer capable of transferring energy to the tissues or to the other components inside or outside the cell. Most preferably, the hapten is a fluorescent dye with absorption and emission maxima in the region of 450–950 nm.

The carrier is selected from the group consisting of proteins such as albumins and globulins, glycoproteins, polypeptides, polysaccharides, polynucleotides, lipoproteins, surfactants, and other natural or synthetic polymeric substances.

Preferably, the carrier is a macromolecule selected from the group consisting of proteins such as albumin or methylated albumin, glycoproteins such as antibodies or selectins, polysaccharides such as inulin or lectins, polynucleotides such as DNA or RNA, inclusion compounds such as cyclodextrins or calixarenes, and surfactants such as Tween. Most preferably the carries is a polysaccharide, polynucleotide, protein, polypeptide, or cyclodextrin.

In a preferred embodiment, a bioconjugate consists of a fluorescent dye hapten with absorption and emission maxima in the region of 450–950 nm and a polysaccharide carrier held together by a non-covalent bond between the dye and the polysaccharide.

In another preferred embodiment, a dye bioconjugate consists of a fluorescent dye hapten with absorption and emission maxima in the region of 450–950 nm and a protein held together by a non-covalent bond between the dye and the protein.

In a further preferred embodiment, a bioconjugate consists of a fluorescent dye hapten with absorption and emission maxima in the region of 450–950 nm and a polypeptide carrier held together by a non-covalent bond between the dye and the polypeptide.

The dye molecules of the present invention may vary widely depending on the contemplated application. For diagnostic imaging of areas of lesion, fluorescent dyes absorbing and emitting in the near infrared (NIR) region, i.e. 700–900 nm, are desirable. These may include, but not limited to, cyanines, indocyanines, or squaraines. For monitoring blood clearance or for endoscopic examination of lesions, dyes absorbing and emitting in the region of 450–950 nm, preferably 600–900 nm, are desirable.

Similarly, the carrier molecules may also vary widely. For blood persistent agents, albumin or methylated serum albumin is preferable. For renal function measurements, a polysaccharide or anionic polypeptides are desirable. For endoscopic examination of lesions, antibodies and antibody fragments are preferred.

The non-covalent carrier-hapten bioconjugates of this present invention can either be advantageously prepared by simply mixing the two components in an optimal stoichiometric proportions and administering an effective amount of this mixture contained in a pharmaceutically acceptable formulation into individuals either systemically or locally to the organ or tissue to be studied. Alternatively, the bioconjugates can be isolated and stored by methods well known in the art. The novel bioconjugates of the present invention have broad clinical utility, which includes, but not limited to, diagnostic imaging of tumors, inflammation (both sterile and bacterial), and impaired vasculature; laser guided endoscopic examination of sites of lesion; photodynamic and chemotherapy of tumors or infection, and dynamic organ function assessment.

The novel bioconjugates of this invention can be formulated into diagnostic or therapeutic compositions for enteral, parenteral, or oral administration. These compositions contain an effective amount of bioconjugates along with conventional pharmaceutical carriers and excipients appropriate for the type of administration contemplated. These compositions may also include stabilizing agents such as ascorbic or gentisic acid, For example, parenteral compositions advantageously contain a sterile aqueous solution or suspension of bioconjugates whose concentration ranges from about 1 μM to about 10 mM. Preferred parenteral formulations have a concentration of bioconjugates of 100 μM to 2 mM. Such solutions also may contain pharmaceutically acceptable buffers and, optionally, electrolytes such as sodium chloride. Formulations for enteral administration may vary widely as is well-known in the art. In general, such formulations are liquids which include an effective amount of bioconjugates in aqueous solution or suspension. Such enteral composition may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired diagnostic or therapeutic objective. Such doses may vary widely depending upon the particular bioconjugates employed, the organs or tissues to be examined, the equipment employed in the clinical procedure, and the like.

The present invention also provides a method of performing a diagnostic or therapeutic procedure on a patient for the purpose of determining the structure and function of tissues or organs. The method comprises administering the non-covalent carrier-hapten bioconjugates of the present invention to a patient, allowing the bioconjugates to become localized in or around a tissue or organ, and performing a diagnostic or therapeutic procedure such as a optical tomographic imaging procedures, fluorescence monitoring procedures, absorbance monitoring procedures, and endoscopic examination procedures, preferably a fluorescence monitoring procedure on the patient.

The present invention also provides a method for altering the blood persistence of a hapten by forming the non-covalent carrier-hapten bioconjugates of the present invention. Some bioconjugates are more stable in vivo than the hapten alone and are cleared from the patient's blood at a slower rate than the hapten alone. The slow blood clearance rate provides more time for doing a diagnostic and therapeutic medical procedure because the hapten remains in the blood system of the patient for an extended period. Other bioconjugates are less stable in vivo than the hapten alone and are cleared from the patient's blood at a faster rate than the hapten alone. The faster blood clearance rate requires less time for doing a diagnostic and therapeutic medical procedure because the hapten remains in the blood system of the patient for a shorter period. This means that the patient can spend less time having the procedure and recuperating.

The present invention also provides a method for increasing the in vitro and in vivo fluorescent life of a fluorescent dye by forming the non-covalent carrier-hapten bioconjugates of the present invention. The bioconjugates retain the ability to fluoresce for extended periods when compared to the fluorescent dye alone. This longer fluorescent life permits the bioconjugates to be stored on the shelf for extended periods and then used for diagnostic and therapeutic medical procedures.

The present invention also provides fluorescent dye bioconjugates that have a longer in vitro and in vivo fluorescent life that the fluorescent dye alone. This longer fluorescent life permits the bioconjugates to be stored on the shelf for extended periods and then used for diagnostic and therapeutic medical procedures.

The following examples illustrate the specific embodiment of the invention described in this document. As would be apparent to skilled artisans, various changes and modifications are possible and are contemplated within the scope of the invention described.

EXPERIMENTAL PROCEDURES

EXAMPLE 1

Blood Clearance Properties of Indocyanine Green Dye

Indocyanine Green Dye

Figure 1:
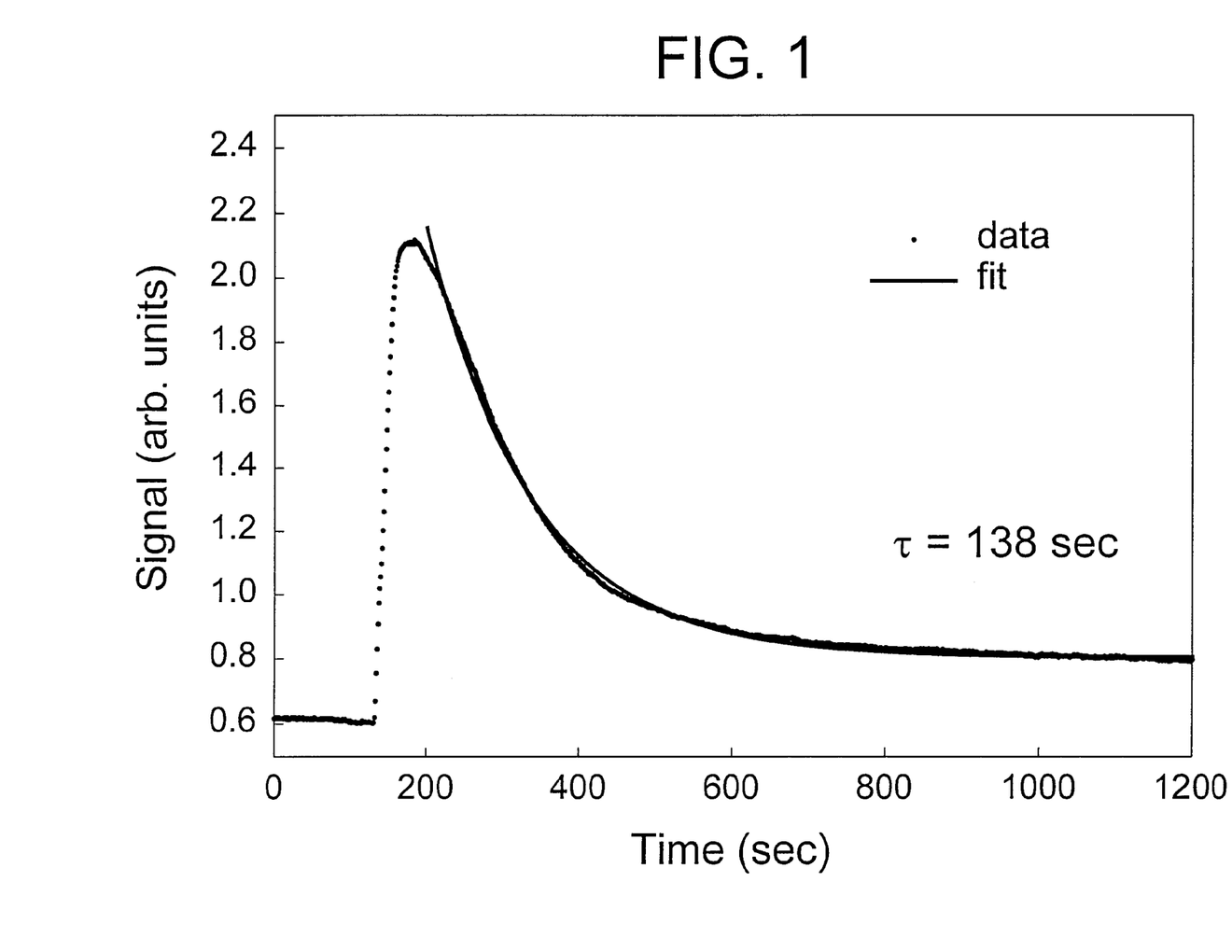
FIG. 1 shows the rat blood clearance rate for indocyanine green dye.

A 500 μL portion of indocyanine green solution (0.8 mg/mL) was injected through the lateral tail vein of Sprague-Dawley or Fischer rats. Blood clearance of the dye bioconjugate was monitored by fluorescence signal emanating from the capillaries of the ear surface using a laser fluorescence apparatus (excitation, 780 nm; emission 830 nm). The time constant (τ) for indocyanine green blood clearance is 138 seconds FIG. 1).

EXAMPLE 2

Figure 2:
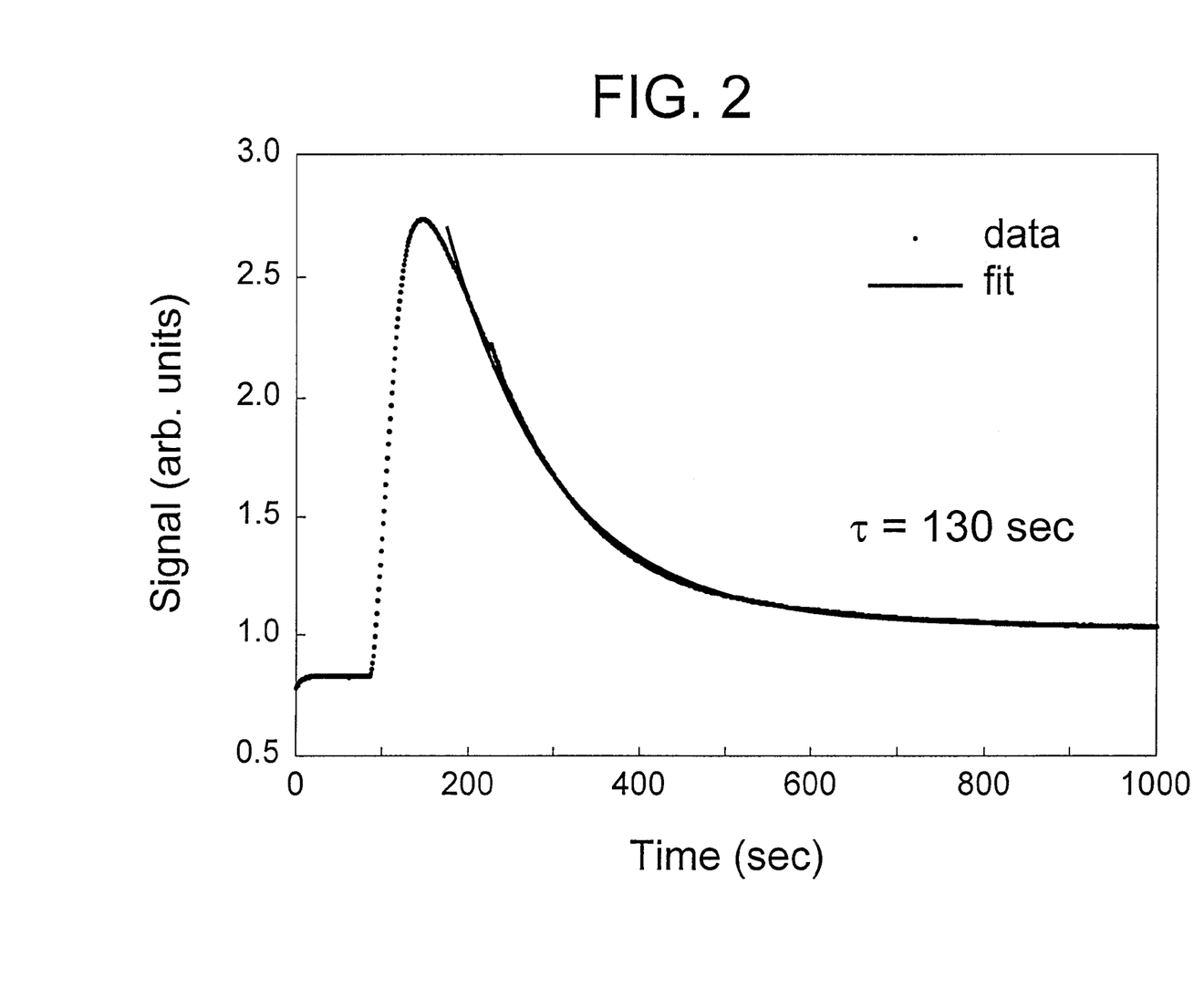
FIG. 2 shows the rat blood clearance rate for an inulin-indocyanine green dye bioconjugate.

Preparation and Blood Clearance Properties of a Inulin-indocyanine Green Dye Bioconjugate A solution of inulin (MW 5000, 30 mg) in water (5 mL) was treated with indocyanine green (4 mg) and the entire mixture was shaken vigorously for about 2 minutes. The blood clearance rate of this bioconjugate was determined using the same procedure described in Example 1. The time constant (τ) for blood clearance for this bioconjugate is 130 seconds (FIG. 2). The blood clearance rate for this bioconjugate is approximately the same as that for indocyanine green.

EXAMPLE 3

Figure 3:
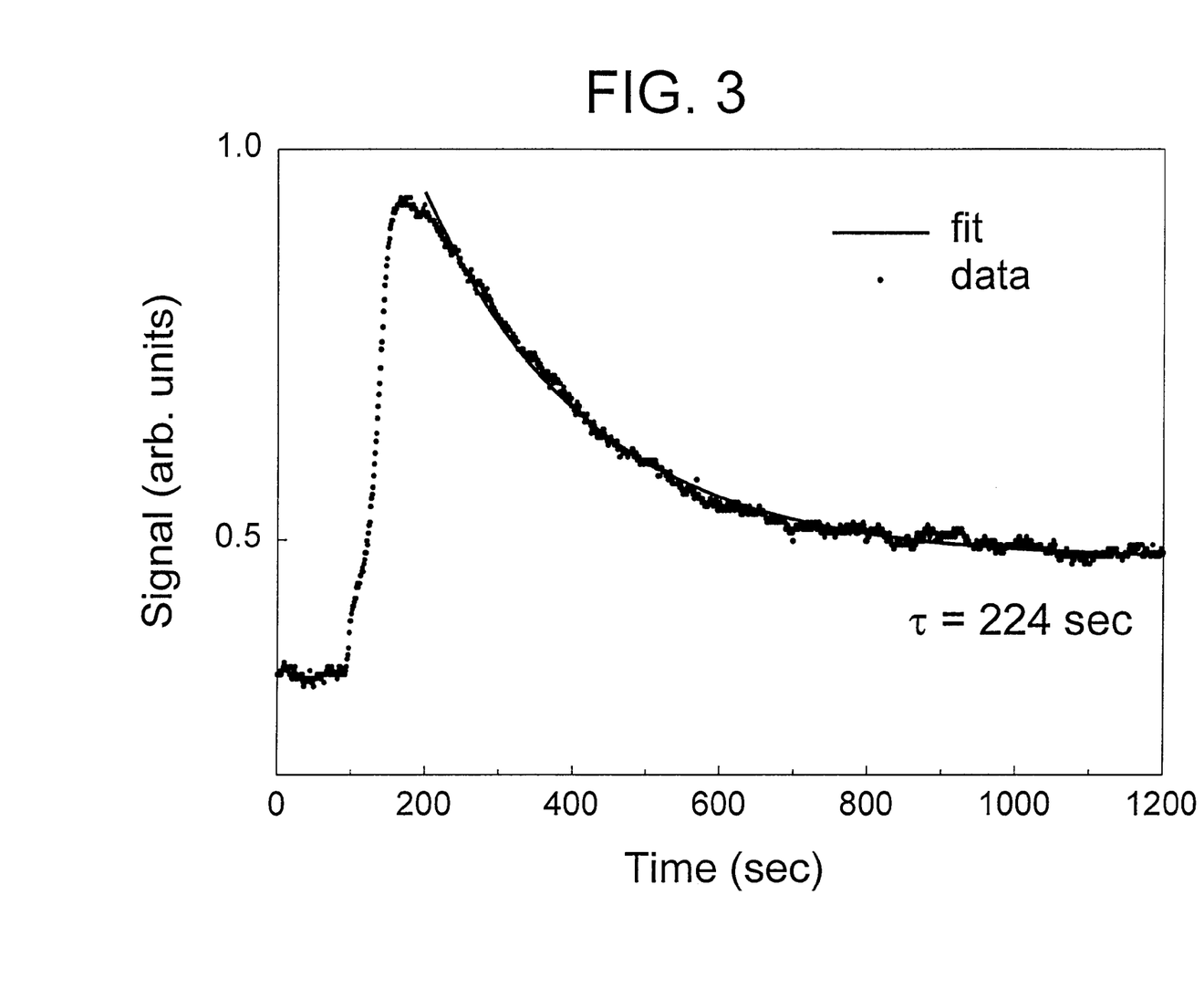
FIG. 3 shows the rat blood clearance rate for a MBSA-indocyanine green dye bioconjugate.

Preparation and Blood Clearance Properties of a MBSA-indocyanine Green Dye Bioconjugate A solution of methylated bovine serum albumin (MBSA) (MW 70000, 25 mg) in water (5 mL) was treated with indocyanine green (4 mg) and the entire mixture was shaken gently for about 5 minutes. The blood clearance rate of this bioconjugate was determined using the same procedure described in Example 1. The time constant (τ) for blood clearance for this bioconjugate is 224 seconds (FIG. 3). The blood clearance rate of this bioconjugate is approximately two times slower than that of indocyanine green.

EXAMPLE 4

Figure 4:
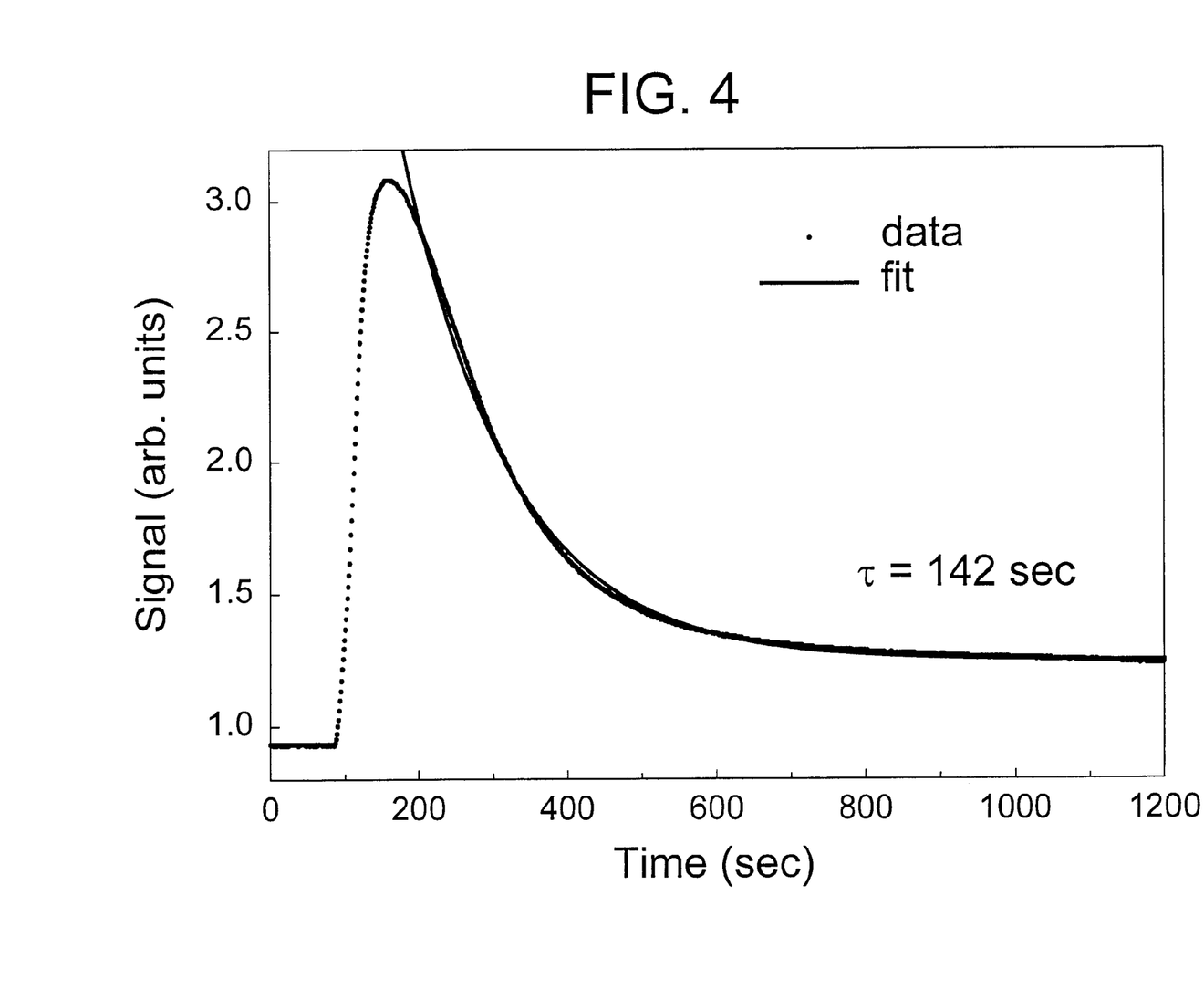
FIG. 4 shows the rat blood clearance rate for a gamma cyclodextrin-indocyanine green dye bioconjugate.

Preparation and Blood Clearance Properties of a Gamma Cyclodextrin-indocyanine Green Dye Bioconjugate A solution of γ-cyclodextrin (MW 1100, 11.2 mg) in water (5 mL) was treated with indocyanine green (4 mg) and the entire mixture was shaken gently for 1 hour. The blood clearance rate of this bioconjugate was determined using the same procedure described in Example 1. The time constant (τ) for blood clearance for this bioconjugate is 142 seconds (FIG. 4). The blood clearance rate of this bioconjugate is approximately the same as that for indocyanine green.

EXAMPLE 5

Figure 5:
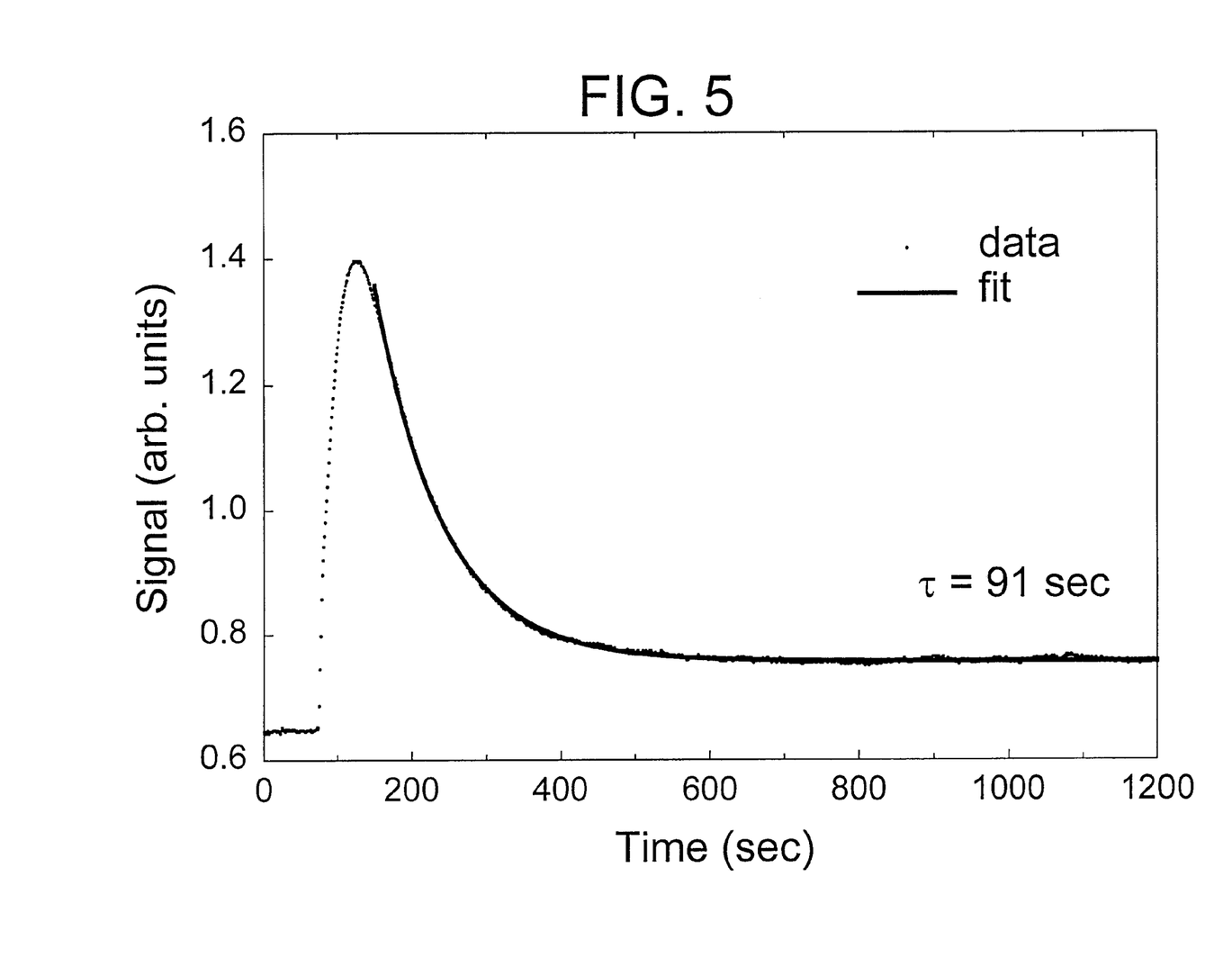
FIG. 5 shows the rat blood clearance rate for a polyaspartic acid-indocyanine green dye bioconjugate.
Figure 6A:
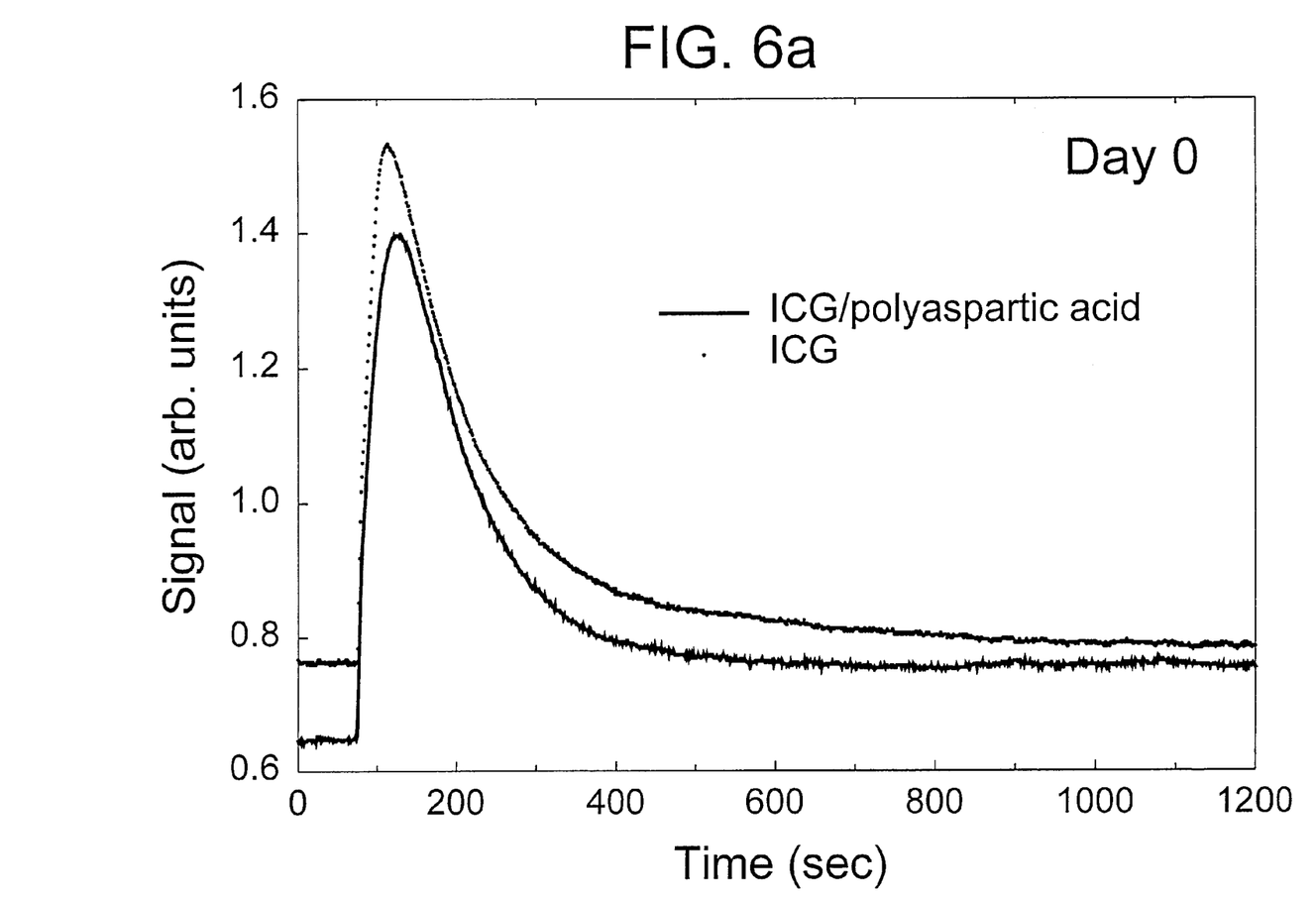
FIG. 6(a) shows the rat blood clearance rate for the polyaspartic-indocyanine green dye bioconjugate and for indocyanine green dye alone at the time of initial preparation in aqueous solution.
Figure 6B:
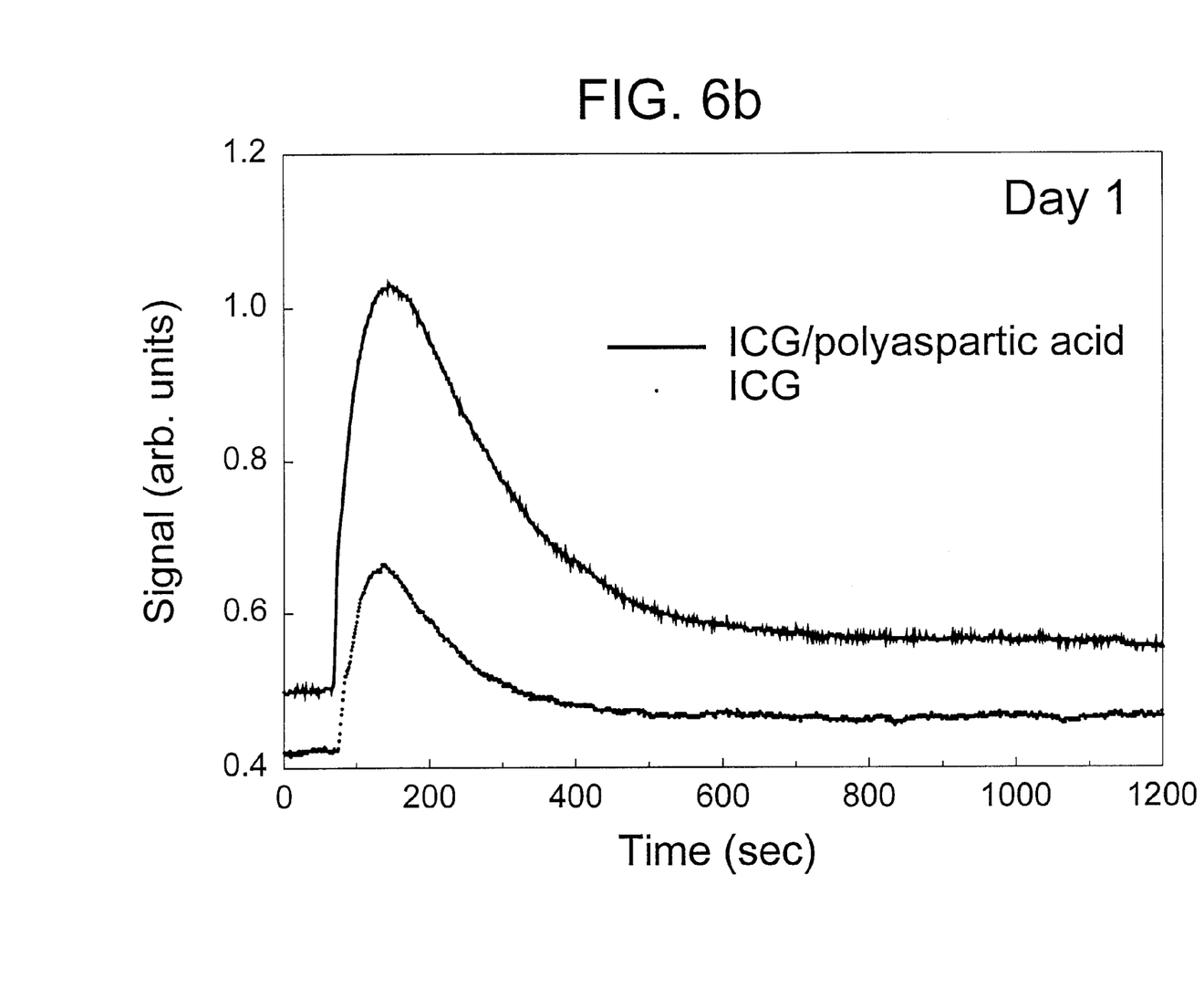
FIG. 6(b) shows the rat blood clearance rate for the polyaspartic-indocyanine green dye bioconjugate and for indocyanine green dye alone at one (1) day after preparation.
Figure 6C:
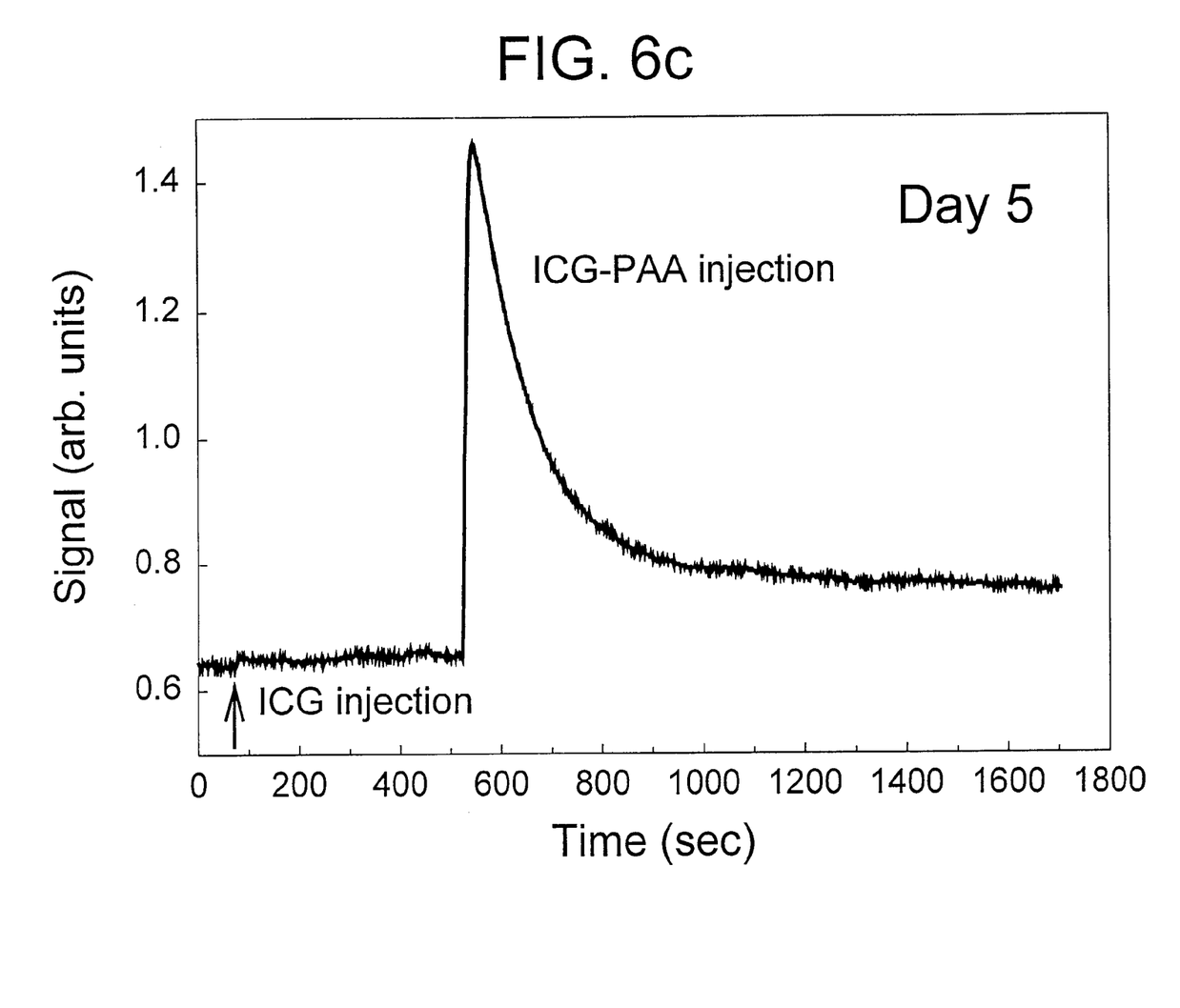
FIG. 6(c) shows the rat blood clearance rate for the polyaspartic-indocyanine green dye bioconjugate and for indocyanine green dye alone at five (5) days after preparation.
Figure 6D:
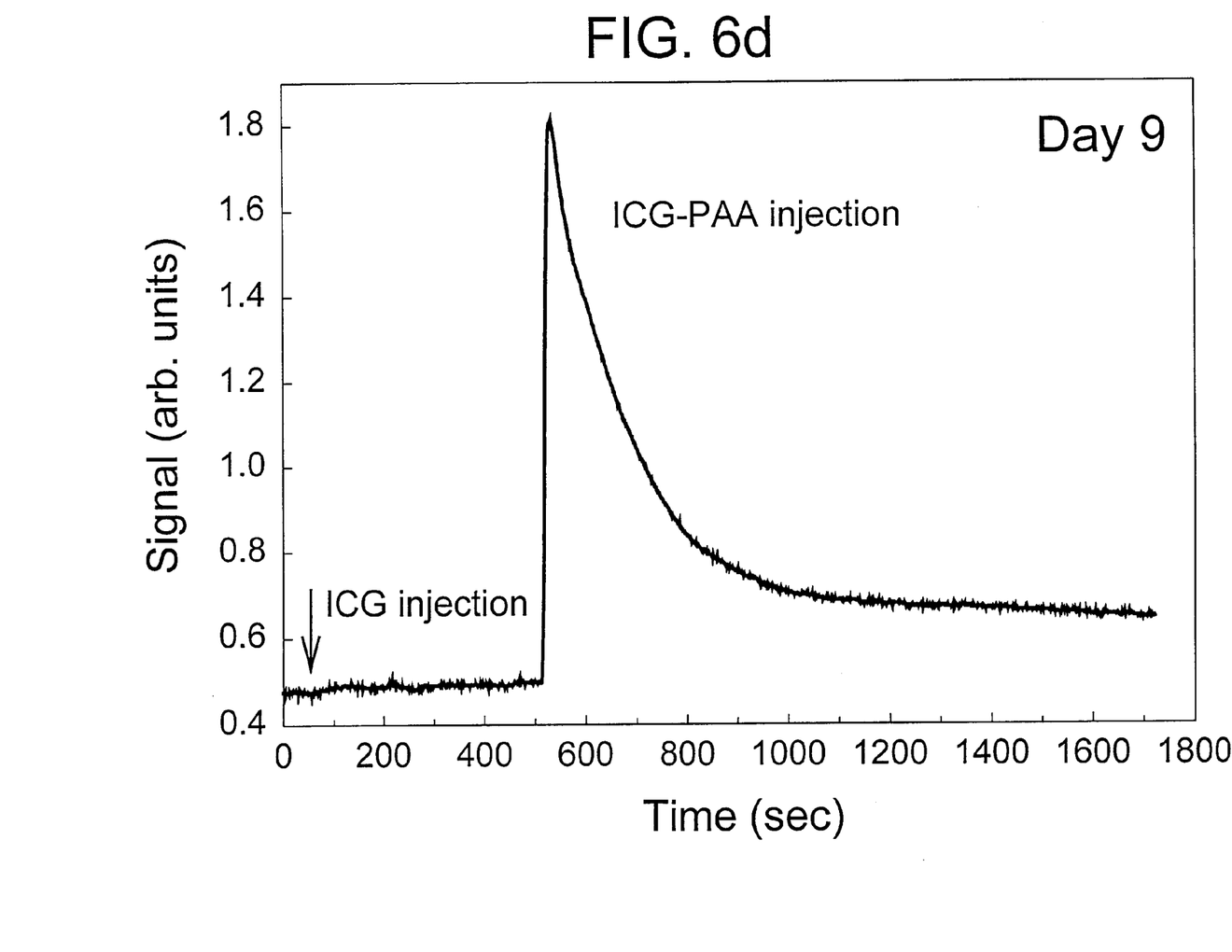
FIG. 6(d) shows the rat blood clearance rate for the polyaspartic-indocyanine green dye bioconjugate and for indocyanine green dye alone at nine (9) days after preparation.

Preparation and Blood Clearance Properties of Polyaspartic Acid-indocyanine Green Dye Bioconjugate A solution of polyaspartic acid (MW 6000, 82 mg) in water (10 mL) was treated with indocyanine green (4 mg) and the entire mixture was shaken gently for about 5 minutes. The blood clearance rate of this bioconjugate was determined using the same procedure described in Example 1. The time constant (τ) for blood clearance for this bioconjugate is 91 seconds (FIG. 5). The blood clearance rate of this bioconjugate is faster than that for indocyanine green.

Referring to Examples 1–5, the data shows that various carriers such as albumins, globulins, glycoproteins, polypeptides, polysaccharides, polynucleotides, lipoproteins, and surfactants interact with indocyanine green dye to form non-covalent carrier-hapten bioconjugates and that the blood persistence of a hapten is altered when in the form of a bioconjugate.

EXAMPLE 6

Stability and Photophysical Properties of Several Indocyanine Green Dye Bioconjugates An aqueous solution of indocyanine green (ICG) and the carriers, inulin, poly-d,l-aspartic acid, polyguanylic acid, MBSA, and γ-cyclodextrin were prepared and the fluorescence intensity was monitored at ambient temperature at various time intervals. Table 1 and FIGS. 6(a), 6(b), 6(c), and 6(d) show the stability data of the bioconjugates.

TABLE 1

Percent decrease in fluorescence intensity at 822 nanometers

| Indocyanine Green Dye | Percent Decrease in Fluorescence | | |
|---|---|---|---|
| | 2 Hours | 4 Hours | 24 Hours |
| Water | 0 | 19 | 48 |
| Inulin | 45 | 45 | 45 |
| Polyaspartic acid | 0 | 0 | 0 |
| γ-Cyclodextrin | 0 | 100 | — |
| MBSA | 0 | 0 | — |
| Polyaspartic acid/BSA | 0 | 0 | 0 |
| Polyguanylic acid | 0 | 0 | 0 |

Referring to FIGS. 6(a), 6(b), 6(c), and 6(d), the data show the stability enhancement achieved by the polyaspartic acid-indocyanine green dye bioconjugate over that of the indocyanine green dye alone. Referring to Table 1, the data show that some stability enhancement is also seen for bioconjugates involving MBSA and polyguanylic acid.

EXAMPLE 7

Preparation of Carboxyphloroglucinol-squaraine Dye

A mixture of 2,4,6-trihydroxybenzoic acid (3.40 g, 0.02 mol) and squaric acid (1.14 g, 0.01 mol) in glacial acetic acid (15 mL) was heated under reflux for 4 hours. The cherry-red solution was poured onto water (100 mL) and the purple dye was collected by filtration, washed well with copious water, and dried. The dye was suspended in water (100 mL) and heated to boiling for about 10 minutes, filtered hot, and dried. The dye was then used as such for further studies (A. Treibs and K. Jacob., *Angew. Chem. Int. Ed. English*, 1965, 4, 694).

EXAMPLE 8

Stability and Photophysical Properties of Several Carboxyphloroglucinol-squaraine Dye Bioconjugates Carboxyphloroglucinol Squaraine Dye An aqueous solution of carboxyphloroglucinol-squaraine dye and the carriers, inulin, poly-l-arginine, poly-d,l-aspartic acid, and γ-cyclodextrin were prepared and the fluorescence was temporally monitored at ambient temperature over 48 hours ($\lambda_{ex}$=515, $\lambda_{em}$=613). The results are shown in Table 2.

TABLE 2

Percent decrease in fluorescence intensity at 613 nanometers

| Carboxyphloroglucinol Squaraine Dye | Percent Decrease in Fluorescence | | |
| --- | --- | --- | --- |
| | 2 Hours | 4 Hours | 24 Hours |
| Water | 13 | 13 | 50 |
| Inulin | 0 | 0 | 5 |
| Polyarginine | 8 | 20 | 43 |
| Polyaspartic acid | 41 | 55 | 55 |
| γ-Cyclodextrin | 27 | 37 | 41 |

Referring to Table 2, the data show that various carriers such as polysaccharides, inclusion compounds, and polynucleotides interact with carboxyphloroglucinol squaraine dye non-covalent carrier-hapten bioconjugates and that the in vitro and in vivo fluorescent life of the fluorescent dye is increased when in the form of a bioconjugate

EXAMPLE 9

Preparation of Benzothiazolim-squaraine Dye

A mixture of 2-methylbenzothiazole (2.98 g, 0.020 mol) and bromoacetic acid (2.98 g, 0.022 mol) was heated to about 100° C. for 15 minutes. The dark reaction mixture was poured onto acetone (100 mL) and the lavender colored solid was collected by filtration, washed with acetone, and dried. A mixture of this benzothiazolium salt (1.38 g, 5 mmol) and squaric acid (0.28 g, 2.5 mmol) in n-butanol/toluene (1:1, 15 mL) was heated under Dean-Stark conditions for 4 hours. The dark blue solution was poured onto water (100 mL) and the blue dye was collected by filtration, washed well with copious acetone, and dried (S. Das et al., *J Phys. Chem.*, 1996, 100, 17310–17315).

EXAMPLE 10

Stability and Photophysical Properties of Benzothiazolim-squaraine Dye Bioconjugates Benzothiazolium Squaraine Dye An aqueous solution of benzothiazolim-squaraine dye and the carriers, inulin, polyarginine, poly-d,l-aspartic acid, polyguanydylic acid, and γ-cyclodextrin were prepared and the fluorescence was temporally monitored at ambient temperature over 48 hours. The results are shown in Table 3.

TABLE 3

Percent decrease in fluorescence intensity at 665 nanometers

| Benzothiazolim Dye | Percent Decrease in Fluorescence | | |
| --- | --- | --- | --- |
| | 2 Hours | 4 Hours | 24 Hours |
| Water | 92 | 64 | 46 |
| Inulin | 92 | 54 | 54 |
| Polyarginine | 0 | 0 | 47 |
| Polyaspartic acid | 0 | 0 | 0 |
| γ-Cyclodextrin | 33 | 41 | 41 |

Referring to Table 3, the data show that various carriers such as polysaccharides, inclusion compounds, and polynucleotides interact with benzothiazolium squaraine dye non-covalent carrier-hapten bioconjugates and that the in vitro and in vivo fluorescent life of the fluorescent dye is increased when in the form of a bioconjugate.

EXAMPLE 11

Preparation of Cyanine Blue Dye Conjugates

Cyanine Blue Dye

A mixture of 2-methylbenzothiazole (2.98 g, 0.020 mol) and bromoacetic acid (2.98 g, 0.022 mol) was heated to about 100° C. for 15 minutes. The dark reaction mixture was poured onto acetone (100 mL) and the lavender colored solid was collected by filtration, washed with acetone, and dried. A mixture of this benzothiazolium salt (1.44 g, 5 mmol) and malonaldehyde tetramethyl acetal (0.42 g, 2.5 mmol) in pyridine was heated under reflux for 4 hours. The dark blue solution was poured onto ether (500 mL) and the blue dye was collected by filtration, washed well with copious ether, and dried.

EXAMPLE 12

Stability and Photophysical Properties of Cyanine Blue Dye Conjugates

An aqueous solution of cyanine blue dye and the carriers, inulin, polyarginine, poly-d,l-aspartic acid, and γ-cyclodextrin were prepared and the fluorescence was temporally monitored at ambient temperature over 24 hours. The results are shown in Table 4.

TABLE 4

Percent decrease in fluorescence intensity at 670 nanometers

| Cyanine Blue Dye | Percent Decrease in Fluorescence | | |
|---|---|---|---|
| | 2 Hours | 4 Hours | 24 Hours |
| Water | 20 | 42 | 99 |
| Inulin | 6 | 10 | 16 |
| Polyarginine | 0 | 0 | 0 |
| Polyaspartic acid | 73 | 73 | 78 |
| γ-Cyclodextrin | 0 | 9 | 9 |

Referring to Table 4, the data show that various carriers such as polysaccharides, inclusion compounds, and polynucleotides interact with cyanine blue dye non-covalent carrier-hapten bioconjugates and that the in vitro and in vivo fluorescent life of the fluorescent dye is increased when in the form of a bioconjugate.

Although the invention has been described with respect to specific modifications, the details thereof are not to be construed as limitations, for it will be apparent that various equivalents, changes, and modifications may resorted to without departing from the spirit and scope thereof, and it is understood that such equivalent embodiments are to be included therein.

What is claimed is:

1. A composition comprising non-covalent carrier-hapten bioconjugates having the formula:

HM-CM wherein HM is a hapten molecule selected from the group consisting of peptides, carbohydrates, photosensitizers, and fluorescent dyes; CM is a carrier molecule selected from the group consisting of proteins, glycoproteins, polypeptides, polysaccharides, inclusion compounds, polynucleotides, lipoproteins, and surfactants; and the dashed line is a non-covalent bond between the carrier molecule and the hapten molecule.

2. The composition of claim 1 wherein HM is selected from the group consisting of peptides containing 10 or less amino acids, oligosaccharides containing 10 or less furanose or pyranose moieties, photosensitizers with absorption and emission maxima in the range of 200–1200 nm, and fluorescent dyes with absorption and emission maxima in the range of 200–1200 nm.

3. The composition of claim 1 wherein CM is selected from the group consisting of serum albumin, methylated bovine albumin, polypeptides having a molecular weight of from 2000 to 20000 Daltons, polysaccharides having a molecular weight of from 2000 to 20000 Daltons, polynucleotides having a molecular weight of from 2000 to 100000 Daltons, cyclodextrins, calixarenes, and surfactants.

4. The composition of claim 1 wherein HM is selected from the group consisting of fluorescent dyes with absorption and emission maxima between 450–950 nm.

5. The composition of claim 4 wherein CM is selected from the group consisting of serum albumin, methylated serum albumin, polypeptides with a molecular weight of from 2000 to 20000 Daltons, and polysaccharides with a molecular weight of from 2000 to 20000 Daltons, polynucleotides, cyclodextrins, calixarenes, and surfactants.

6. The composition of claim 4 wherein HM is selected from the group consisting of cyanine, indocyanine, squaraine, porphyrrins, Rose Bengal, and methylene blue dye.

7. The composition of claim 6 wherein CM is selected from the group consisting of methylated serum albumin, polyarginine, polyaspartic acid, polyglutamic acid, cyclodextrin, and inulin.

8. A method of performing a diagnostic or therapeutic procedure on a patient, comprising:
  administrating to a patient a diagnostic or therapeutic effective amount of non-covalent carrier-hapten bioconjugates having the formula:

HM-CM wherein HM is a hapten molecule selected from the group consisting of peptides, carbohydrates, photosensitizers, and fluorescent dyes; CM is a carrier molecule selected from the group consisting of proteins, glycoproteins, polypeptides, polysaccharides, inclusion compounds, polynucleotides, lipoproteins, and surfactants; and the dashed line is a non-covalent bond between the carrier molecule and the hapten molecule;
  allowing the bioconjugates to become localized in or around a tissue or organ; and
  performing a diagnostic or therapeutic procedure on the patient.

9. The method of claim 8 wherein said procedure is selected from the group of optical tomographic imaging procedures, fluorescence monitoring procedures, absorbance monitoring procedures, and endoscopic examination procedures.

10. The method of claim 8 wherein HM is selected from the group consisting of peptides containing 10 or less amino acids, oligosaccharides containing 10 or less furanose or pyranose moieties, photosensitizers with absorption and emission maxima in the range of 200–1200 nm, and fluorescent dyes with absorption and emission maxima in the range of 200–1200 nm.

11. The method of claim 8 wherein CM is selected from the group consisting of serum albumin, methylated bovine albumin, polypeptides having a molecular weight of from 2000 to 20000 Daltons, polysaccharides having a molecular weight of from 2000 to 20000 Daltons, and polynucleotides having a molecular weight of from 2000 to 100000 Daltons, polynucleotides, cyclodextrins, calixarenes, and surfactants.

12. The method of claim 8 wherein HM is selected from the group consisting of fluorescent dyes with absorption and emission maxima between 450–950 nm.

13. The method of claim 8 wherein CM is selected from the group consisting of serum albumin, methylated serum albumin, polypeptides with a molecular weight of from 2000 to 20000 Daltons, and polysaccharides with a molecular weight of from 2000 to 20000 Daltons, polynucleotides, cyclodextrins, calixarenes, and surfactants.

14. The method of claim 8 wherein said procedure is a fluorescence monitoring procedure.

15. The method of claim 14 wherein HM is selected from the group consisting of cyanine, indocyanine, squaraine, porphyrrins, Rose Bengal, and methylene blue dye.

16. The method of claim 15 wherein CM is selected from the group consisting of methylated serum albumin, polyarginine, polyaspartic acid, polyglutamic acid, cyclodextrin, and inulin.

17. A method of for altering the blood persistence of a hapten comprising forming non-covalent carrier-hapten bioconjugates having the formula:

HM-CM wherein HM is a hapten molecule selected from the group consisting of peptides, carbohydrates, photosensitizers, and fluorescent dyes; CM is a carrier molecule selected from the group consisting of proteins, glycoproteins, polypeptides, polysaccharides, polynucleotides, lipoproteins, and surfactants; and the dashed line is a non-covalent bond between the carrier molecule and the hapten molecule.

18. The method of claim 17 wherein HM is selected from the group consisting of peptides containing 10 or less amino acids, oligosaccharides containing 10 or less furanose or pyranose moieties, photosensitizers with absorption and emission maxima in the range of 200–1200 nm, and fluorescent dyes with absorption and emission maxima in the range of 200–1200 nm.

19. The method of claim 17 wherein CM is selected from the group consisting of serum albumin, methylated bovine albumin, polypeptides having a molecular weight of from 2000 to 20000 Daltons, polysaccharides having a molecular weight of from 2000 to 20000 Daltons, and polynucleotides having a molecular weight of from 2000 to 100000 Daltons, polynucleotides, cyclodextrins, calixarenes, and surfactants.

20. The method of claim 17 wherein HM is selected from the group consisting of fluorescent dyes with absorption and emission maxima between 450–950 nm.

21. The method of claim 20 wherein CM is selected from the group consisting of serum albumin, methylated serum albumin, polypeptides with a molecular weight of from 2000 to 20000 Daltons, and polysaccharides with a molecular weight of from 2000 to 20000 Daltons, polynucleotides, cyclodextrins, calixarenes, and surfactants.

22. The method of claim 20 wherein HM is selected from the group consisting of cyanine, indocyanine, squaraine, porphyrrins, Rose Bengal, and methylene blue dye.

23. The method of claim 22 wherein CM is selected from the group consisting of methylated serum albumin, polyarginine, polyaspartic acid, polyglutamic acid, cyclodextrin, and inulin.

24. A method of increasing the in vitro and in vivo fluorescent life of a fluorescent dye comprising forming non-covalent carrier-hapten bioconjugates having the formula:

HM-CM wherein HM is a hapten molecule selected from the group consisting of fluorescent dyes; CM is a carrier molecule selected from the group consisting of proteins, glycoproteins, polypeptides, polysaccharides, inclusion compounds, polynucleotides, lipoproteins, and surfactants; and the dashed line is a non-covalent bond between the carrier molecule and the hapten molecule.

25. The method of claim 24 wherein HM is selected from the group consisting of fluorescent dyes with absorption and emission maxima in the range of 200–1200 nm.

26. The method of claim 24 wherein CM is selected from the group consisting of serum albumin, methylated bovine albumin, polypeptides having a molecular weight of from 2000 to 20000 Daltons, polysaccharides having a molecular weight of from 2000 to 20000 Daltons, and polynucleotides having a molecular weight of from 2000 to 100000 Daltons, polynucleotides, cyclodextrins, calixarenes, and surfactants.

27. The method of claim 24 wherein HM is selected from the group consisting of fluorescent dyes with absorption and emission maxima between 450–950 nm.

28. The method of claim 27 wherein CM is selected from the group consisting of serum albumin, methylated serum albumin, polypeptides with a molecular weight of from 2000 to 20000 Daltons, and polysaccharides with a molecular weight of from 2000 to 20000 Daltons, polynucleotides, cyclodextrins, calixarenes, and surfactants.

29. The method of claim 27 wherein HM is selected from the group consisting of cyanine, indocyanine, squaraine, porphyrrins, Rose Bengal, and methylene blue dye.

30. The method of claim 29 wherein CM is selected from the group consisting of methylated serum albumin, polyarginine, polyaspartic acid, polyglutamic acid, cyclodextrin, and inulin.

\* \* \* \* \*